United States Patent
Kofinas et al.

(10) Patent No.: US 9,863,886 B2
(45) Date of Patent: Jan. 9, 2018

(54) COLOR CHANGING POLYMER FILMS FOR DETECTING CHEMICAL AND BIOLOGICAL TARGETS

(71) Applicants: University of Maryland, College Park, College Park, MD (US); The United States of America as Represented by the Secretary of the Army, Washington, DC (US)

(72) Inventors: Peter Kofinas, North Bethesda, MD (US); Omar B. Ayyub, Potomac, MD (US); Jennifer W. Sekowski, Forest Hill, MD (US); Ta-I Yang, North Potomac, MD (US)

(73) Assignees: University of Maryland, College Park, College Park, MD (US); The United States of America as Represented by the Secretary of the Army, Washington, DC (US)

( * ) Notice: Subject to any disclaimer, the term of this patent is extended or adjusted under 35 U.S.C. 154(b) by 47 days.

(21) Appl. No.: 14/804,755

(22) Filed: Jul. 21, 2015

(65) Prior Publication Data
US 2016/0018337 A1    Jan. 21, 2016

Related U.S. Application Data

(62) Division of application No. 13/484,533, filed on May 31, 2012, now Pat. No. 9,115,240.

(60) Provisional application No. 61/492,728, filed on Jun. 2, 2011.

(51) Int. Cl.
| | |
|---|---|
| *G01N 21/78* | (2006.01) |
| *C08F 293/00* | (2006.01) |
| *C08F 8/44* | (2006.01) |
| *G01N 21/77* | (2006.01) |

(52) U.S. Cl.
CPC .............. *G01N 21/78* (2013.01); *C08F 8/44* (2013.01); *C08F 293/00* (2013.01); *G01N 2021/7723* (2013.01); *Y10T 436/143333* (2015.01); *Y10T 436/144444* (2015.01); *Y10T 436/173076* (2015.01); *Y10T 436/206664* (2015.01)

(58) Field of Classification Search
None
See application file for complete search history.

(56) References Cited

U.S. PATENT DOCUMENTS

| | | | |
|---|---|---|---|
| 5,849,839 | A | 12/1998 | Hubbell et al. |
| 7,550,271 | B2 | 6/2009 | Patton et al. |
| 2002/0026937 | A1 | 3/2002 | Mault |
| 2003/0003494 | A1 | 1/2003 | Ogura et al. |
| 2006/0134796 | A1 | 6/2006 | Bommarito et al. |
| 2007/0297994 | A1 | 12/2007 | Wendland et al. |

OTHER PUBLICATIONS

Ayyub, O.B. et al. (2011) "*Color Changing Block Copolymer Films for Chemical Sensing of Simple Sugars*," Biosensors Bioelectronics 28:349-354.
Bates et al (1990) "*Block Copolymer Thermodynamics: Theory and Experiment*," Ann. Rev. Phys. Chem. 41:525-557.
Bielecki et al. (1999) *A Fluorescent Glucose Sensor Binding Covalently to All Five Hydroxyl Groups of A-D-Gluiofuranose A Reinvestigation*, J. Amer. Chem. Soc.: Perkin Transactions 2(3):449-455.
Bosch et al. (2004) "*Binary and Ternary Phenylboronic Acid Complexes With Saccharides and Lewis Bases*," Tetrahedron 60(49): 11175-11190.
Chen et al. (2009) "*Polyvinylamine-Phenylboronic Acid Adhesion to Celluslose Hydrogel*," Langmuir 25(12):6863-6868.
Cui et al. (2009)"*Photonic Crystal Borax Competitive Binding Carbohydrate Sensing Motif*," Analyst 134(5):875-880.
Endo et al. (2010) "*Reflectometric Detection of Influenza Virus in Human Saliva Using Nanoimprint Llithography-Based Flexible Two-Dimensional Photonic Crystal Biosensor*," Sensors and Actuators B: Chemical 148(1):269-276.
Germain, M.E. et al. (2009) "*Optical Explosives Detection: From Color Changes to Fluorescence Turn-on*," Chem. Soc. Rev. 38:2543-2555.
Kang, Y. et al. (2007) "*Broad-Wavelength-Range Chemically Tunable Block Copolymer Photonic Gels*," Nature Materials, 957-960 (2007).
Kim et al. (2007) "*Sugar Sensing Based on Induced pH Changes*," Chemical Communications 22:2299-2301.
Lee, K. et al. (2000) "*Photonic Crystal Chemical Sensors:pH and Ionic Strength*," J. Amer. Chem Soc. 122(39):9534-9537.
Lee, M. et al. (2007) "*Two-Dimensional Silicon Photonic Crystal Based Biosensing Platform for Protein Detection*," Optics Express 15 (8), 4530-4535.
Li et al. (2003) "*Polymer Replicas of Photonic Porous Silicon for Sensing and Drug Delivery Applications*," Science 299(5615):2045-2047.
Sekowski, J et al. (2010)"*Biotic-Abiotic Interfaces Within a Nanostructured Polymer Matric Platform: Towards a Completely Abiotic System*," Edgewood Chemical Biol. Center In-House Laboratory Independent Res. Program, Annual Report FY10 (86 pages).
Springsteen, G. et al. (2002) "*A Detailed Examination of Boronic Acid-Diol Complexation*," Tetrahedron 58(26):5291-5300.

*Primary Examiner* — Karen Cochrane Carlson
*Assistant Examiner* — Jennifer M. H. Tichy
(74) *Attorney, Agent, or Firm* — William C. Schrot; AuerbachSchrot LLC

(57) ABSTRACT

A sensor system, and a method of detecting a target analyte, comprises a chemically functionalized block copolymer, and a target analyte. The block copolymer exhibits a color change in the visible spectrum upon exposure to the target analyte.

9 Claims, 16 Drawing Sheets
(4 of 16 Drawing Sheet(s) Filed in Color)

COLOR CHANGING POLYMER FILMS FOR DETECTING CHEMICAL AND BIOLOGICAL TARGETS

CROSS-REFERENCE TO RELATED APPLICATIONS

This application is a divisional of U.S. patent application Ser. No. 13/484,533, filed May 31, 2012, which application is based on U.S. Patent Application Ser. No. 61/492,728, filed Jun. 2, 2011, entitled "Color Changing Polymer for Chemical/Biological Threat and Pathogen Detection," which applications are incorporated herein by reference in their entireties and to which priority is claimed.

STATEMENT REGARDING FEDERALLY SPONSORED RESEARCH OR DEVELOPMENT

This work was supported by the US Army ECBC ILIR Program as provided for by the terms of W911SR08C0031. This work was also supported by the National Science Foundation Grant No. CBET0947771. The US government has certain rights in this invention.

FIELD OF THE INVENTION

The present invention relates to a sensor system that exhibits a visible change upon exposure to a target, and in particular, a chemically functionalized block copolymer film that exhibits a color change in the visible light spectrum upon exposure to a target analyte.

BACKGROUND OF THE INVENTION

Conventional sensor systems have been developed from various materials that change color upon exposure to a target molecule. Such sensor systems are generally based on photonic crystals that have been modified to recognize the target molecule. The photonic crystal contains periodic nanostructures with differing indices of refraction that interact with visible light. The material recognizes or binds to specific chemical targets. Recognition of the target alters the spacing of the periodic nanostructure, thereby changing the way it interacts with visible light.

The advantage of such systems lies in producing a discernable change in color. This concept has been applied in the fabrication of colloidal hydrogel systems, porous silicon systems, as well as through the use of lithography techniques on other substrates. The use of a photonic crystal polymerized colloidal hydrogel system has been demonstrated (Cui et al. (2009) Analyst 134(5):875-880; Lee, K., Asher, S. A. (2000) Journal of the American Chemical Society 122(39): 9534-9537. Such material could act as a sensor for glucose but required the complex process of synthesizing monodisperse, highly charged polystyrene particles. Porous silicon (Lee, M., Fauchet, P. M. (2007) Optics Express 15 (8), 4530-4535; Li et al. (2003) Science 299(5615): 2045-2047) and nanoprint lithography (Endo et al. (2010) Sensors and Actuators B: Chemical 148(1):269-276) have also been reported as photonic crystal chemical sensing platforms. The observed response in such conventional systems, however, is small, non-visible, and thus cannot be measured without the aid of supplementary equipment and further analytical measurements.

Therefore, there is a need for a sensor that can be easily fabricated, and yield an instantaneous, visibly discernable response.

SUMMARY OF THE INVENTION

The present invention is directed to hybrid biotic/abiotic structures fabricated using chemically functionalized block copolymers, such as Polystyrene-b-poly(2-vinyl pyridine) (PS-b-P2VP) block copolymers. The polymer films of the present invention induce a visible color change when exposed to aqueous media.

In disclosed embodiments, the P2VP block of the copolymer may be functionalized with either 2-bromomethylphenylboronic acid or bromoethylamine. In one implementation, the 2-bromomethylphenylboronic acid functionalization allows the polymer films to respond to glucose with a change in color. For example, when exposed to glucose the color of the film may be changed from green to orange.

In one implementation, ovalbumin antibodies are attached to films functionalized with bromoethylamine. These films respond to the ovalbumin protein with a color change. This functionalization may be further modulated to detect foodborne pathogens, such as *Escherichia coli, Listeria, Salmonella*, warfare agents such as Ricin, Sarin or Soman, or HMEs such as nitroglycerin or TATP. The polymer coating undergoes a color change in the visible light spectrum, providing manufacturers, consumers, and vendors with a facile method for identifying such analytes.

A sensor system according to one embodiment of the disclosed invention comprises a chemically functionalized block copolymer, and a target analyte. The block copolymer exhibits a color change in the visible spectrum when exposed to the target analyte. In one implementation, the block copolymer has a lamellar morphology or structure.

In one embodiment, the functionalized block copolymer is a polystyrene-b-poly(2-vinyl pyridine) (PS-b-P2VP) block copolymer. In one implementation, the P2VP block of the copolymer is functionalized with 2-bromomethylphenylboronic acid or bromoethylamine.

In one embodiment, the target analyte is a sugar, such as for example, glucose, fructose, galactose and mannose. In another embodiment, the target analyte is a foodborne pathogen, such as for example *Escherichia coli, Listeria*, or *Salmonella*. In another embodiment, the target analyte is a toxin, such as for example, ricin, sarin, or soman. In another embodiment, the target analyte is an explosive compound, such as for example nitroglycerin or triacetone triperoxide. In another embodiment, the target analyte is a component of human sweat.

In one embodiment, an antibody is linked to the functionalized block copolymer, wherein the antibody binds to the target analyte. In one implementation, the antibody is polyclonal ovalbumin antibody.

In one embodiment the functionalized block copolymer is coupled to a textile or fabric material. In one implementation, the resulting textile material exhibits a shift in color change upon exposure to human sweat.

A method of detecting a target analyte according to an embodiment of the present invention comprises the steps of: providing a block copolymer; functionalizing the block copolymer; and exposing the functionalized block copolymer to a target analyte, whereby the functionalized block copolymer exhibits a color change in the visible light spectrum upon exposure to the target analyte.

In one embodiment of the disclosed method, the block copolymer is 2-vinyl pyridine. The 2-vinyl pyridine block copolymer may be functionalized with 2-bromomethylphenylboronic acid or bromoethylamine.

The present invention is also directed to a chemically functionalized block copolymer. The functionalized block copolymer exhibits a shift in peak wavelength in the visible light spectrum upon exposure to a target molecule. In one implementation, the shift in peak wavelength is at least about 40 nm. In one implementation, the shift in peak wavelength is at least about 200 nm.

BRIEF DESCRIPTION OF THE DRAWINGS

The file of this patent contains at least one drawing/photograph executed in color and that copies of this patent with color drawing(s)/photograph(s) will be provided by the Office upon request and payment of the necessary fee.

DETAILED DESCRIPTION OF THE INVENTION

Figure 1:
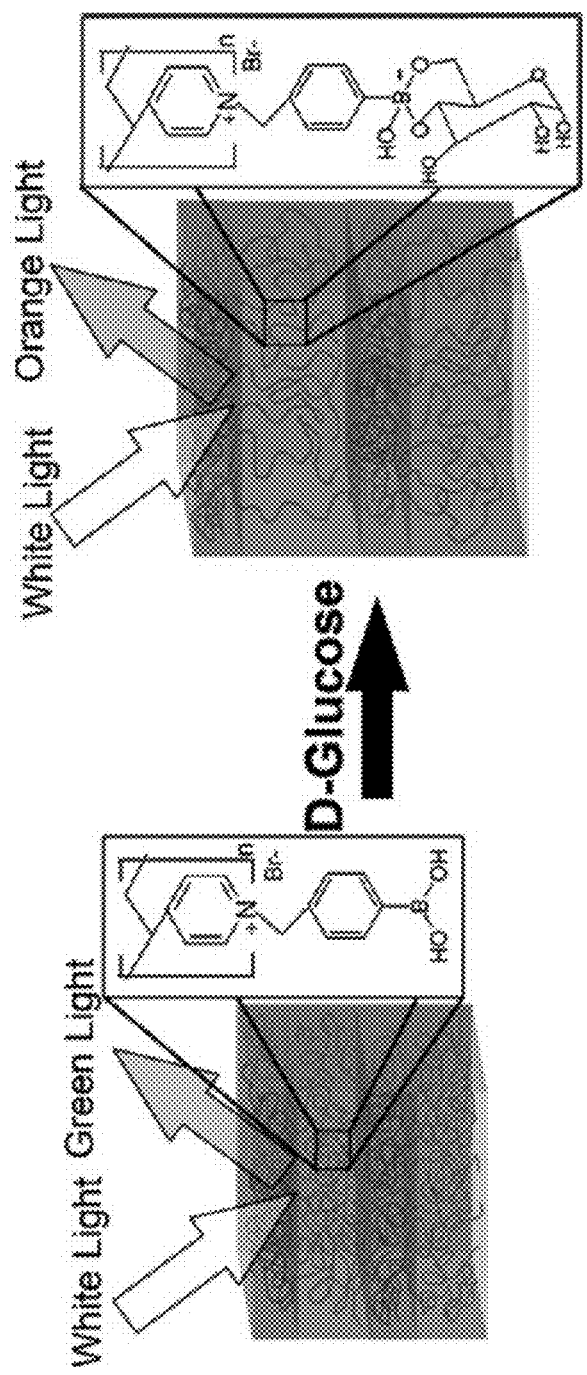
FIG. 1 is a schematic of a BCP film sensor according to an embodiment of the present invention.

The present invention is directed to a polymeric material capable of specifically and selectively recognizing a variety of distinct targets, such as foodborne pathogens, chemical and biological warfare agents, and homemade explosives (HMEs). The disclosed material may be in form of a flexible polymer film or coating, which may be applied to food packaging, provided as a litmus test strip, configured as small "stickers" or large coating sheets, or integrated into fabric. Upon selective recognition of a target, for example foodborne pathogens such as *Escherichia coli, Listeria, Salmonella*, warfare agents such as Ricin, Sarin or Soman, or HMEs such as nitroglycerin or triacetone triperoxide (TATP), the polymer material undergoes a color change in the visible light spectrum providing manufacturers, consumers, and vendors with a facile method for identifying any of these analytes or other selected targets.

The visible light spectrum (or visible spectrum or visible light) is the portion of the electromagnetic spectrum that is visible to the human eye. Generally, a human eye will respond to and perceive wavelengths from about 390 to 750 nm (corresponding to a band in the vicinity of 400-790 THz). The visible color change in the visible spectrum of block copolymers is triggered by changes in swelling conditions of the material. The recognition properties, stability and reusability of known binding moieties specific to each analyte create a simple and reliable nanostructured polymer material or coating providing utility in a wide variety of applications.

In order to create a polymeric material that can successfully recognize a desired biological or chemical molecule, a selective recognition element is combined with a measurable output signal. According to an embodiment of the present invention, the disclosed materials achieve these needs by utilizing the tunable reflectance of swollen functionalized block copolymers (BCPs). Block copolymers include two or more chemically distinct sequences of monomer repeat units linked together through a covalent bond. Upon evaporation from a solvent, BCPs will microphase separate into solid films, displaying a number of different morphologies (e.g., hexagonal, cubic, gyroid, lamellar) depending on the relative volume fraction of each block (Bates et al (1990) Annual Review of Physical Chemistry 41:525-557).

BCPs in which both blocks are of equal molecular weight generally exhibit the lamellar morphology. Self-assembly into a lamellar morphology is significant in producing a BCP photonic crystal. If there is enough contrast in refractive index between the two blocks in the lamellar structure, then certain wavelengths of light will be reflected by the material. This phenomenon is dictated by: $\lambda_1 = 2(n_1 d_1 + n_2 d_2)$, where $\lambda_1$ is the reflected wavelength, $n_i$ is the refractive index of layer i and $d_i$ is the thickness of layer i.

In one embodiment, the diblock copolymer polystyrene-b-poly(2-vinylpyridine) (PS-b-P2VP), which microphase separates into a lamellar periodic stack, was utilized for its use as a chemical sensor to detect and respond to glucose with a change in color. The 2-vinyl pyridine (P2VP) block was quaternized with 2-(bromomethyl)phenylboronic acid, which placed a positive charge on the pyridine ring of the block. This charge allows the BCP film to swell in aqueous media. The swelling changes the thickness of the block allowing it to interact with wavelengths of visible light. Lamellar PS-b-P2VP films quaternized with bromoethane place a positive charge in the P2VP block, and attach an ethyl group to the nitrogen atom. The quaternizing agent contributes a boronic acid residue, giving the BCP the ability to bind to sugars such as glucose. Binding induced a change in the distance between the lamellae, causing a change in the wavelength light reflected by the polymer, thus allowing the BCP to act as a glucose sensor.

Boronic acids are of interest in chemical sensing due to their ability to covalently bind to sugar molecules such as glucose (see Bosch et al. (2004) Tetrahedron 60(49): 11175-11190; Chen et al. (2009) Langmuir 25(12):6863-6868; Kim et al. (2007) Chemical Communications 22:2299-2301). Although sensing glucose has applications in diabetic medicine, the utilization of glucose sensing using the boronic acid functionalized BCP system served as a model system to test the concept that block copolymer based photonic crystals can be fabricated to act as chemical sensors for small molecule detection. In the present invention, the polymer film was tested for successful attachment of the boronic acid, retention of the lamellar morphology postfunctionalization, and sensitivity and specificity to simple sugar binding.

A schematic of a BCP film sensor according to an embodiment of the present invention is shown in FIG. 1. Initially, the BCP film is fabricated to exhibit a periodic lamellar stack. The P2VP block of the block copolymer is functionalized with phenylboronic acid placing a positive charge on the pyridine ring, which allows the P2VP block to swell in aqueous media until its thickness is large enough to interact with visible light, in this case reflecting green light. The phenylboronic acid can bind sugars and will do so when exposed to a glucose solution.

As shown in FIG. 1, the boronic acid binds to the 1,3 diol functionality. This is the kinetically favored binding site on glucose as well as the 1,2 cis diol (see Bielecki et al. (1999) Journal of the Chemical Society: Perkin Transactions 2(3): 449-455). This binding event lowers the pKa of the phenylboronic acid causing it to form the negatively charged boronate complex. The negative charge triggers additional swelling of the BCP film, changing its color from green to orange. We have shown that after functionalization, the BCP film can respond to a glucose solution and shows a selective response when exposed to different sugars, such as fructose, mannose or galactose.

Thus, an A-B diblock copolymer that microphase separates into a lamellar periodic stack is utilized. The A block is water-insoluble polystyrene (PS) and does not contain any functional groups on the polymer chain that can interact with the target (e.g., biological/chemical threat compound). The B block contains the 2-vinyl pyridine (P2VP) functionality, which can be further chemically modified to serve as ionic interaction sites with known threat receptors.

Figure 2:
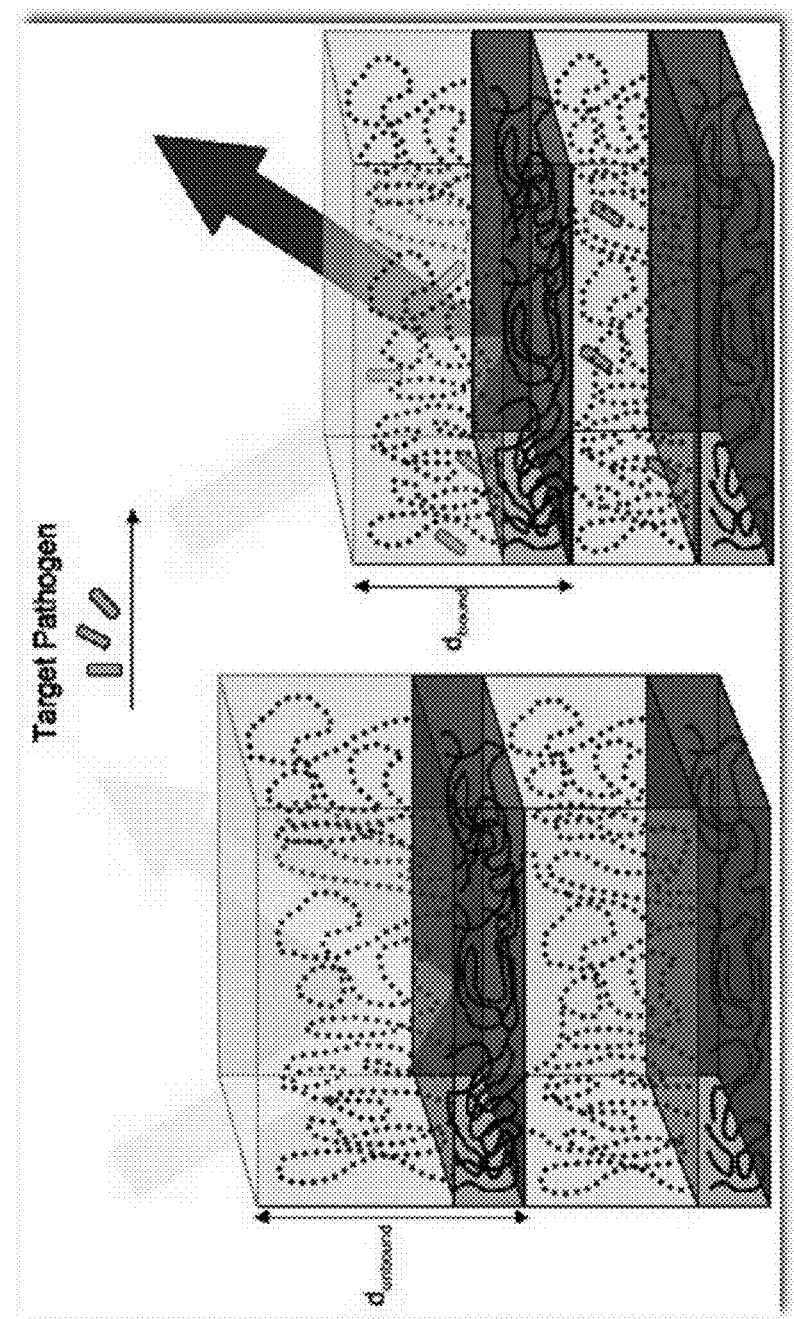
FIG. 2 is a schematic of BCP film according to the present invention, showing the film in an unbound state (shown at the left) and a bound state (shown at the right). The spacing (d) and refractive index contrast between subsequent layers changes when a chemical/biological (CB) agent selectively binds to capture reagent in one of the layers.
Figure 3:
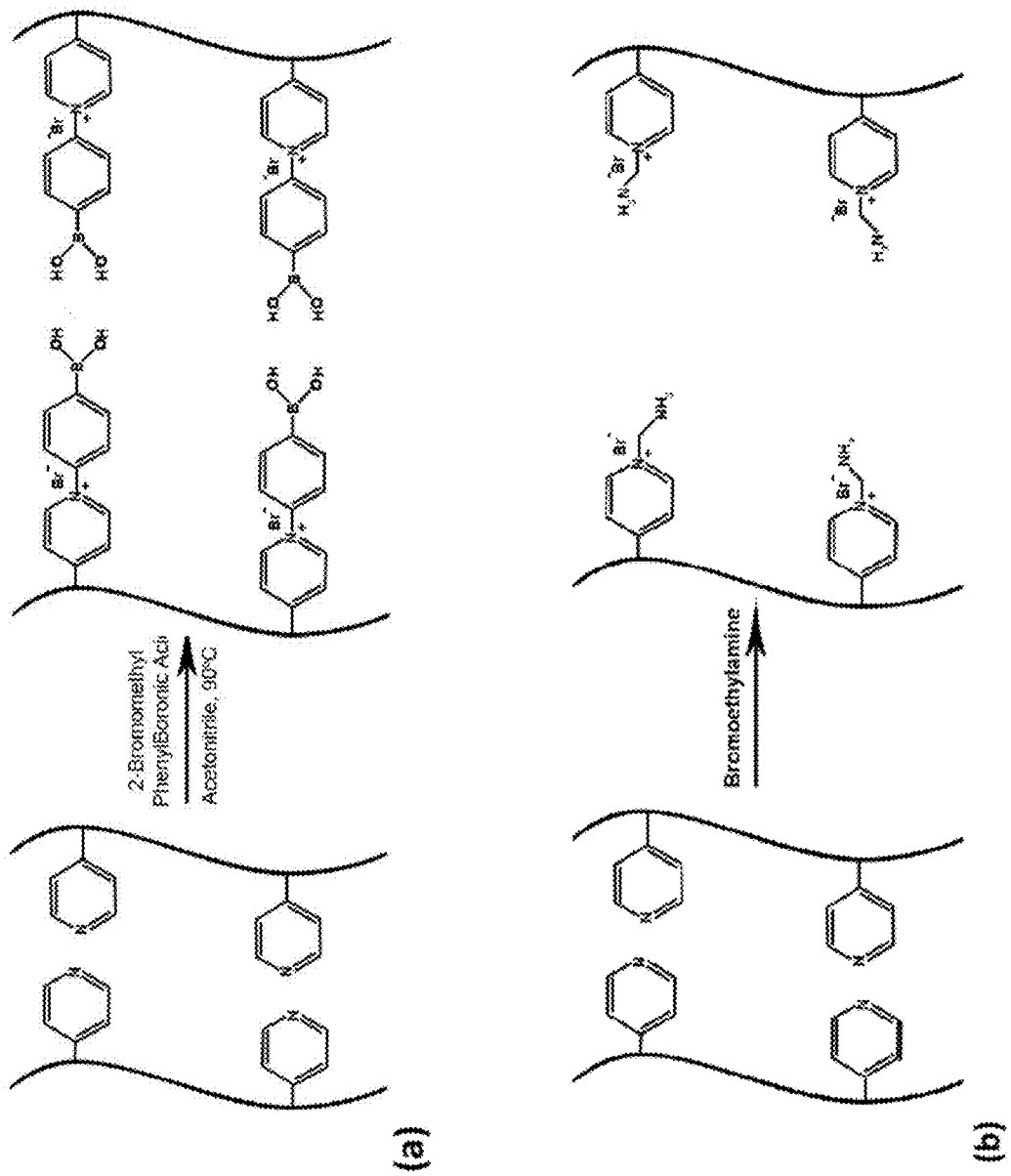
FIG. 3 illustrates the functionalization of the 2-vinyl pyridine block with: 2-Bromomethylphenylboronic acid, shown in FIG. 3(a); and bromoethylamine, shown in FIG. 3(b).

Without modification, the refractive index contrast between subsequent A and B layers is too low to successfully reflect light in the visible wavelength. In addition, the spacing between these layers is not large enough to interact with visible light. Through selective chemical modification of the B block, the condition for visible light can be achieved, thus creating lamellar structures with tunable reflective properties. Upon binding an analyte, the B layers swell, increasing the spacing between the subsequent A layers. In addition, the refractive index contrast between alternating layers is increased. The ranges of wavelengths reflected are highly dependent upon the spacing between the A and B layers, and the refractive indices of subsequent layers. Thus, the color of the self-assembled polymer films may be modulated by simply changing the spacing (d) between subsequent layers, as shown in FIG. 2. This may be achieved by controlling the amount of swelling due to the target pathogen (e.g., biological or chemical) binding event.

With continued reference to FIG. 2, films of the block copolymer polystyrene-b-poly(2-vinyl pyridine) (PS-b-P2VP) may be fabricated to have a periodic lamellar structure. These solid films may then be chemically functionalized. This functionalization only occurs on the poly(2-vinyl pyridine) block of the copolymer, placing a positive charge on the nitrogen atom of the pyridine ring, thereby causing the film to swell in water and change color.

In one implementation, the block copolymer films were functionalized with either 2-bromomethylphenylboronic acid or bromoethylamine, as shown in FIG. 3. The choice of either 2-Bromomethylphenylboronic acid or bromoethylamine depends on the chemical or biological target. The 2-(bromomethyl)phenylboronic acid functionalization allows the films to target sugars (e.g., such as glucose), while the bromoethylamine functionalization allows for further modification of the films.

For example, to functionalize the P2VP block of the copolymer, a solution of 40 mg of either 2-(bromomethyl)phenylboronic acid or bromoethylamine in 40 mL of acetonitrile is prepared. The block copolymer films are then immersed in the solution for 24 hours at 90° C. The 90° C. temperature is a solubility LCST for the PS-b-P2VP in acetonitrile. This temperature prevents the polymer from dissolving in the solvent, thereby permitting functionalization.

When functionalized with the 2-bromomethylphenylboronic acid, the films respond to the sugar glucose with a change in color. The bromoethylamine functionalization places a primary amine along the poly-2-vinyl pyridine block. The primary amine may then have antibodies for proteins, such as Ricin, attached to the polymer film. When exposed to Ricin, the CB agent will bind to the antibody causing the polymer film to swell and change color. In one implementation, polyclonal ovalbumin antibodies are attached to the polymer films, and the films are then exposed to the ovalbumin protein. The films respond with a change in color, as described above.

In another implementation, the functionalized block copolymer material is integrated into or coupled to a fabric material. The resulting fabric material may be integrated into a shirt or other article of clothing, and change color when exposed to a selected target substance. For example, a shirt may include a portion (e.g., such as a company logo or design) including the polymer material integrated therein, which exhibits a change in color in the visible spectrum when exposed to the wearer's sweat, for example a target component of sweat.

Having generally described the invention, the same will be more readily understood through reference to the following examples, which are provided by way of illustration and are not intended to be limiting of the present invention unless specified.

EXAMPLES

The use of functionalized photonic block copolymer films for the detection of glucose was investigated. Polystyrene-b-poly(2-vinyl pyridine) (PS-b-P2VP) block copolymers were chemically functionalized with 2-(bromomethyl)phenylboronic acid and cast into films that reflect a visible color when exposed to aqueous media. The 2-(bromomethyl) phenylboronic acid functionality can reversibly bind to glucose. When exposed to high concentrations of glucose the polymer responded with a red-shift in color. Low concentration exposure of glucose caused the polymer films to blue-shift in color. The BCP films also exhibited a selective response to fructose, mannose or galactose, giving a different response depending on which sugar was present. The color of the polymer was tuned to blue, green, yellow or orange by varying the film's crosslink density. The color change was visually observed without the use of equipment such as a spectrometer.

Fabrication of Photonic BCP Films

The procedure for fabrication of the PS-b-P2VP films was adapted from Kang et al. (2007). The PS-b-P2VP block copolymers were purchased from Polymer Source (Montreal, Canada). The molecular weight of each block of the copolymer was 133,000 g/mol. A 5% weight/volume stock solution of PS-b-P2VP was prepared in propylene glycol monomethyl ether acetate (PGMEA). The solution was then passed through a 0.2 μm teflon filter and degassed under vacuum for 10 minutes. The films were prepared by spin-casting 300 μl of the PSb-P2VP solution onto 1"×1" glass slides at 350 rpm for 2 minutes. The glass slides were purchased from Ted Pella (Redding, Calif.), and were functionalized with 3-(aminopropyl)triethoxysilane. The spin-cast block copolymer films were subsequently annealed in chloroform vapor at room temperature (50° C.) for 24 hours to allow them to self-assemble into a lamellar structure.

Functionalization and Tuning of Photonic Properties

The P2VP block of the spincast films was quaternized with 2-(bromomethyl)phenylboronic acid. The quaternization reaction places a phenylboronic acid functional group in the P2VP block, allowing the polymer to bind sugars (e.g., glucose). The quaternization reaction was carried out by immersing the spincast, annealed block copolymer films in a solution of 40 mg of 2-(bromomethyl)phenylboronic acid in 40 ml of acetonitrile and allowing it to reflux for 5 h. The quaternized polymers were then removed from the solution and dried in a 50° C. oven for 1 hour.

To tune the optical properties of BCP film a crosslinking agent, 1,4-dibromo-2-butanol, was introduced into the acetonitrile solution. Different molar ratios of 2-(bromomethyl)phenylboronic acid to 1,4-dibromo-2-butanol were tested at 0.05 mmol as the total monomer amount. The same protocol was used to investigate the effect of different degrees of crosslinking on the color of the BCP films.

Characterization

Fourier transform infrared spectroscopy (FTIR) was utilized to determine whether the boronic acid functionality was successfully attached. The functionalized polymer film was removed from the glass slide by immersion in a 5% v/v aqueous solution of hydrofluoric acid. The freestanding polymer film was dried for 24 hours in a 50° C. oven. An FTIR spectrum was obtained of the functionalized polymer film using a Thermo Nicolet FT-Raman, Model 670 (Thermo Fisher Scientific, Waltham, Mass.). To determine whether the lamellar morphology was maintained after functionalization, images of the polymer were taken using transmission electron microscopy (TEM). The sample was prepared by embedding a section of the functionalized polymer film in Spurr's resin purchased from Ted Pella (Redding, Calif.). The embedded polymer film was then dry microtomed and stained through exposure to solid iodine for 1 hour. The images were taken using a JEM-2100F 200 kV (Jeol Ltd., Tokyo, Japan) transmission electron microscope.

Sugar Detection

Once the films were functionalized with 2-(bromomethyl)-phenylboronic acid, they were exposed to various concentrations of d-glucose to observe if the films would respond with a color change. Aqueous solutions of 50, 40, 30, 10, 5 and 1 mg/ml of d-glucose were prepared. The films were soaked in 20 ml of DI water and a coverslip was placed on top of the polymer film on the glass slide to retain the water in the film as it was transferred to a UV-Visible spectrometer. The water-swollen control sample was then placed in a Perkin Elmer Lambda25 UV-Visible spectrometer and the visible spectrum was measured using UV-Vis spectroscopy. Each film was then soaked in one of the prepared glucose concentrations and the visible spectrum was again measured and compared to the film soaked in pure water. To test for selectivity between glucose and other sugars, films were prepared and exposed to 50 mg/ml solutions of glucose, fructose, galactose and mannose and their visible spectra measured.

Antibody Attachment and Protein Detection

Films quaternized with bromoethylamine were further modified by attaching polyclonal ovalbumin antibodies. The attachment was performed using 1-Ethyl-3-(3-dimethylaminopropyl)carbodiimide (EDC) as well as N-Hydroxysuccinimide (NHS). The ovalbumin antibody was placed in (N-morpholino)ethanesulfonic acid buffer solution using a Slide-A-Lyzer at a concentration of 1 mg/ml. 1.1 mg of NHS and 0.5 µl EDC were added to the solution. The EDC was allowed to bind to the carboxylic acid groups on the antibody for 15 minutes. A film functionalized with bromoethylamine was then immersed in this solution for 3 hours. Once the antibody attachment reaction was complete, the film was introduced to a solution of 30 mg/ml solution of ovalbumin protein.

Before testing each film's response to either ovalbumin or glucose, FTIR was utilized to determine if the functionalizations were successful. Once verified, films with the bromoethylamine functionalization were further modified with ovalbumin antibodies, and then exposed ovalbumin solutions, and observed. Films functionalized with bromomethylphenylboronic acid were placed in various glucose concentrations, and their responses were measured using UV-Vis spectroscopy.

Verification of Bromoethylamine Attachment

Figure 4:
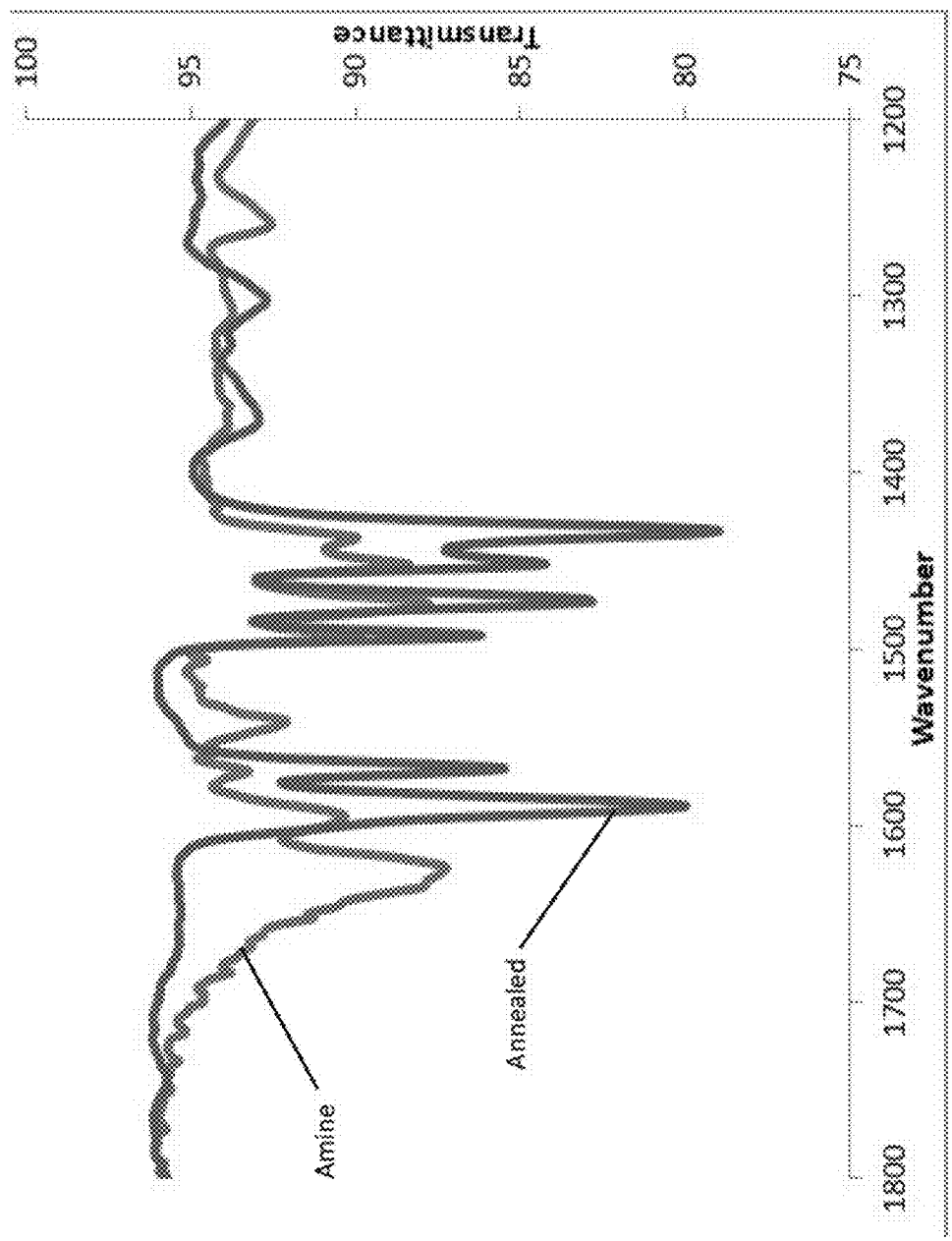
FIG. 4 is a graph showing Fourier transform infrared spectroscopy (FTIR) spectrum data of an unmodified annealed polymer film compared to a film modified with bromoethylamine/bromomethylphenylboronic acid.

To verify that the PS-b-2VP films were functionalized with bromoethylamine, FTIR was utilized to determine functionalization with bromoethylamine (see FIG. 4), as well as antibody attachment.

Detection of Ovalbumin

Figure 5:
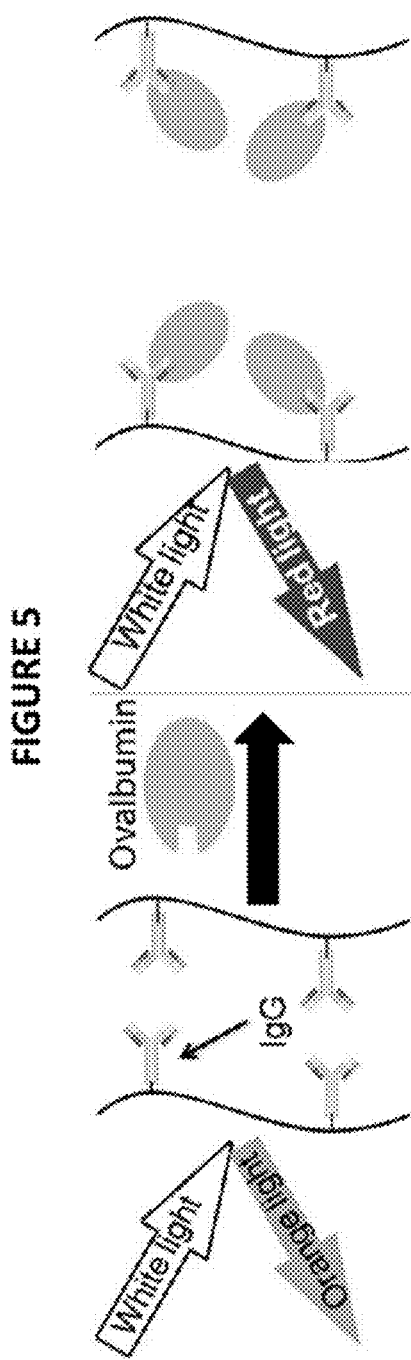
FIG. 5 illustrates schematically PS-b-2VP films quaternized with bromoethylamine and further modified with polyclonal ovalbumin antibody using a carbodiimide reaction. When introduced to ovalbumin protein, the protein binds to the antibody causing a shift in mass and volume in the polymer film, causing the film to swell and change color (from orange to red).
Figure 6:
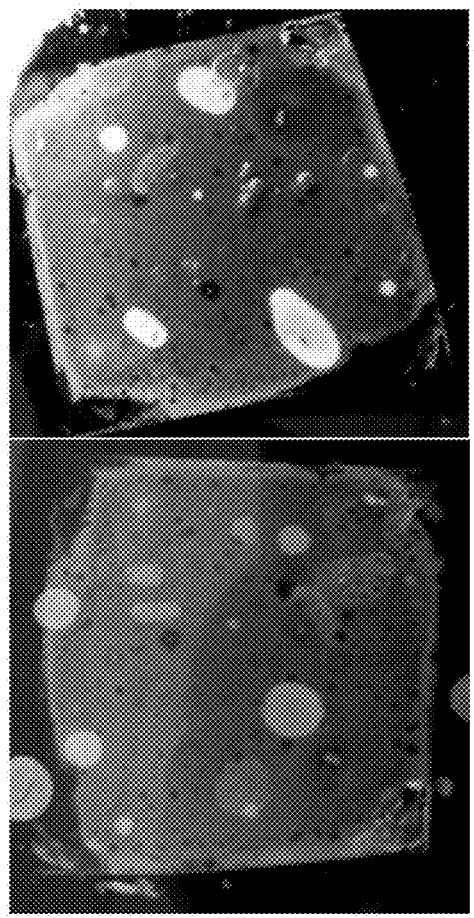
FIG. 6 shows antibody modified PS-b-2VP film having a light orange coloration (left plate) before exposure to protein, and a deep red orange coloration (right plate) after exposure to ovalbumin.

PS-b-2VP films quaternized with bromoethylamine were further modified with polyclonal ovalbumin antibody using a carbodiimide reaction. As illustrated schematically in FIG. 5 and shown in FIG. 6, when introduced to ovalbumin the film swelled, changing its color from light orange to red. This concept may be adapted for other proteins and enzymes, such as antibodies specific to Ricin or peroxidases for the detection of the HME TATP.

Verification of Boronic Acid Attachment

Figure 7:
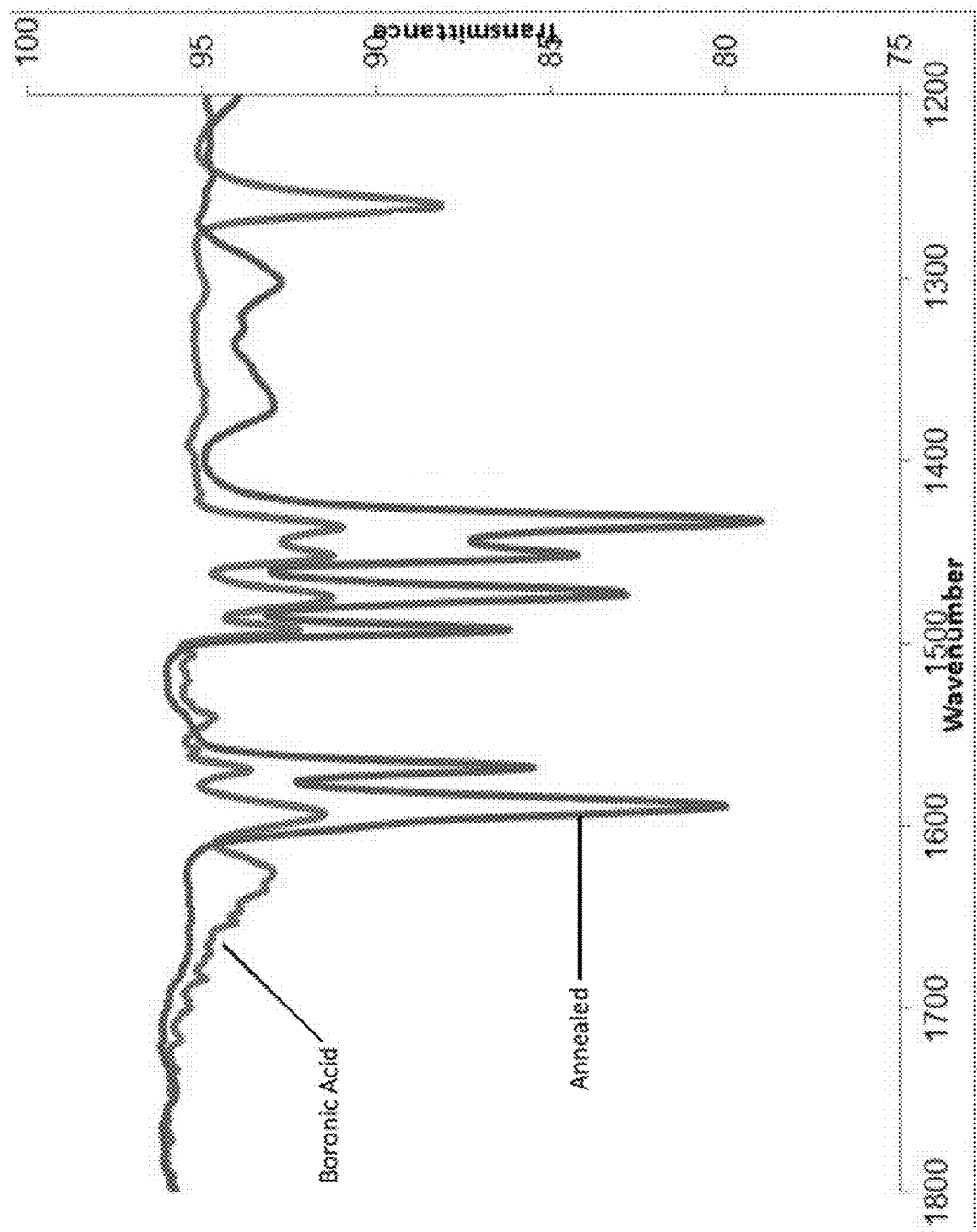
FIG. 7 is a graph showing FTIR spectrum data of an unmodified annealed polymer film compared to a film modified with bromoethylamine/bromomethylphenylboronic acid.

To determine if the 2-(bromomethyl)phenylboronic acid was attached to the glucose sensing polymer, FTIR was utilized (see FIG. 7).

Detection of Glucose

Figure 8:
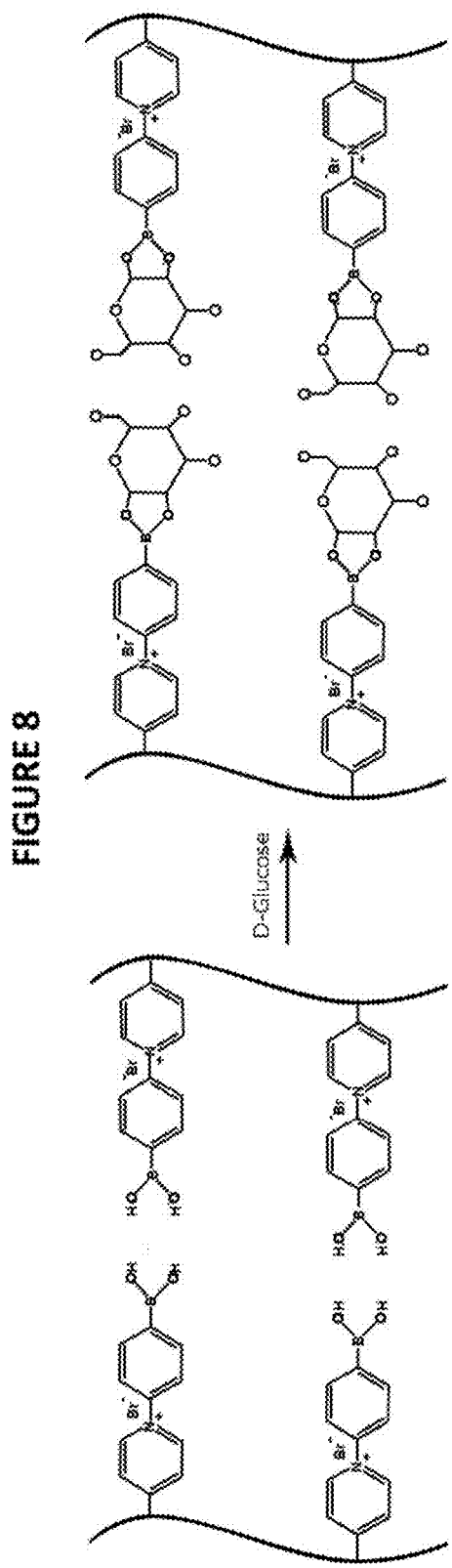
FIG. 8 illustrates schematically the PS-b-2VP film functionalized with 2-Bromomethylphenylboronic acid, whereby the boronic acid groups reversibly bind to each other, cross-linking the film and inhibiting swelling. When exposed to glucose, the boronic acid cross-links are broken as the boronic acid groups bind to glucose, thereby allowing the film to swell.
Figure 9:
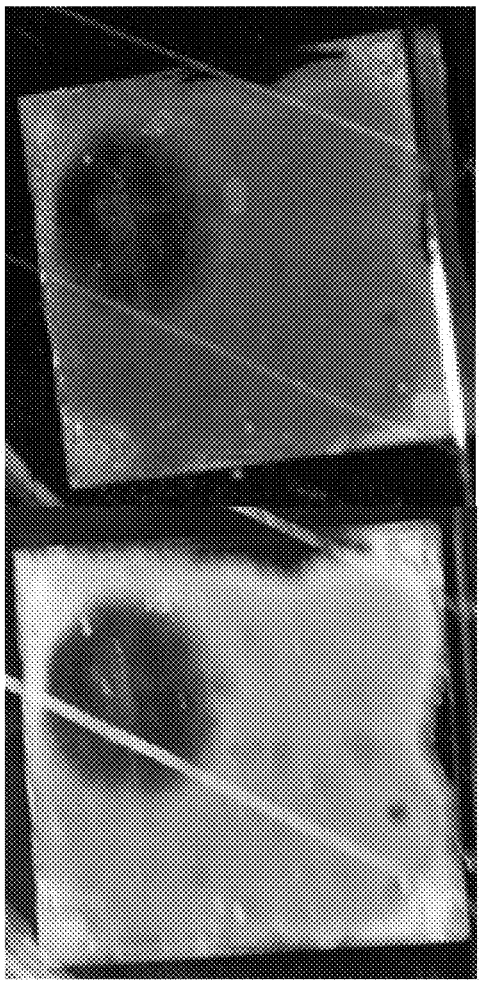
FIG. 9 shows PS-b-2VP film functionalized with 2-Bromomethylphenylboronic acid having a green color (left plate), and an orange color (right plate) after exposure to a 50 mg/ml D-glucose solution.

The PS-b-2VP films functionalized with 2-Bromomethylphenylboronic acid were exposed to a 20 mL 50 mg/mL aqueous solution of D-glucose. The films were initially green in pure deionized water due to the functionalization. Once exposed to the glucose solution the films instantly swelled and became orange in color. This color change and proposed mechanism is illustrated schematically in FIG. 8 and shown in FIG. 9.

Figure 10:
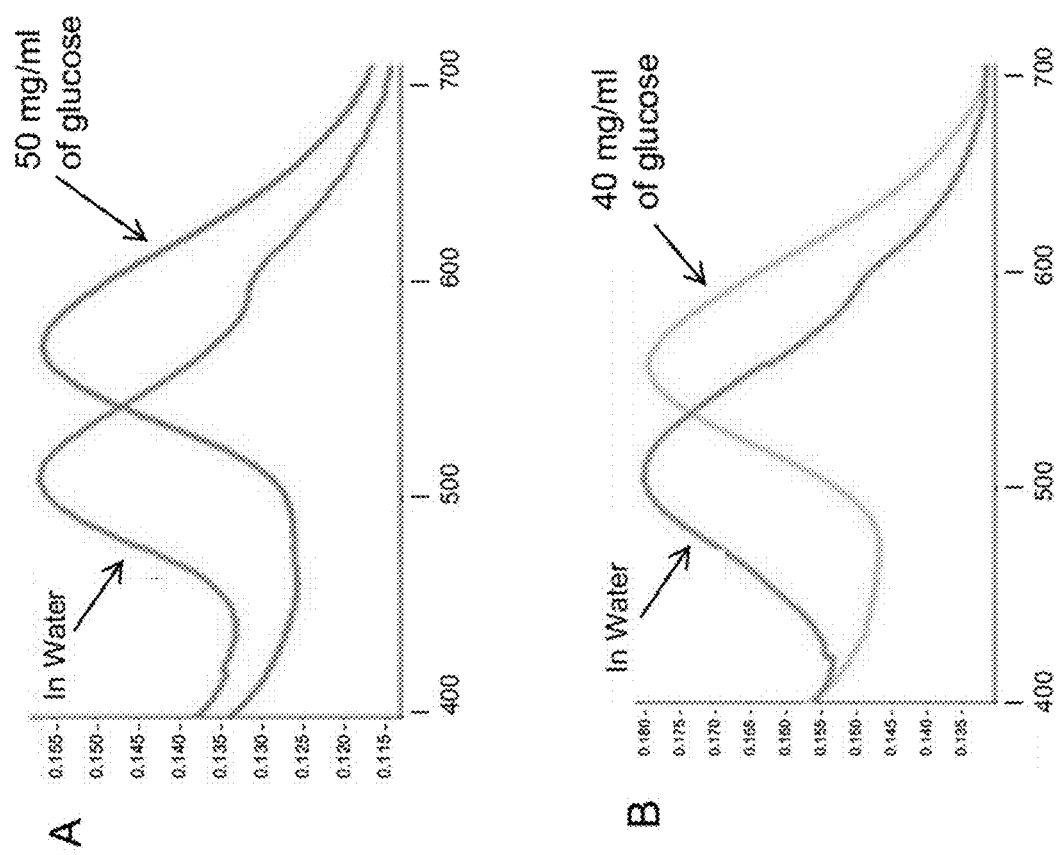
FIG. 10 illustrates graphically the shift in the visible spectrum's peak of the films before and after exposure to glucose measured using Ultraviolet-visible (UV-Vis) spectroscopy. FTIR spectrum data of film in water and in a 50 mg/ml glucose solution is shown in FIG. 10A; FTIR spectrum data of film in water and a 40 mg/ml glucose solution is shown in FIG. 10B.

Films were exposed to various aqueous concentrations of glucose. To show a change in color, the visible spectrum of the films before and after exposure to glucose was measured using UV-Vis spectroscopy. The spectrum's peak shifted toward 700 nm or the "red" end of the spectrum after exposure, as shown in FIGS. 10A and 10B. When exposed to concentrations of 50 mg/ml and 40 mg/ml glucose solutions, the films shifted from green to orange, or green to yellow, respectively. This indicates that they became swollen.

Figure 11:
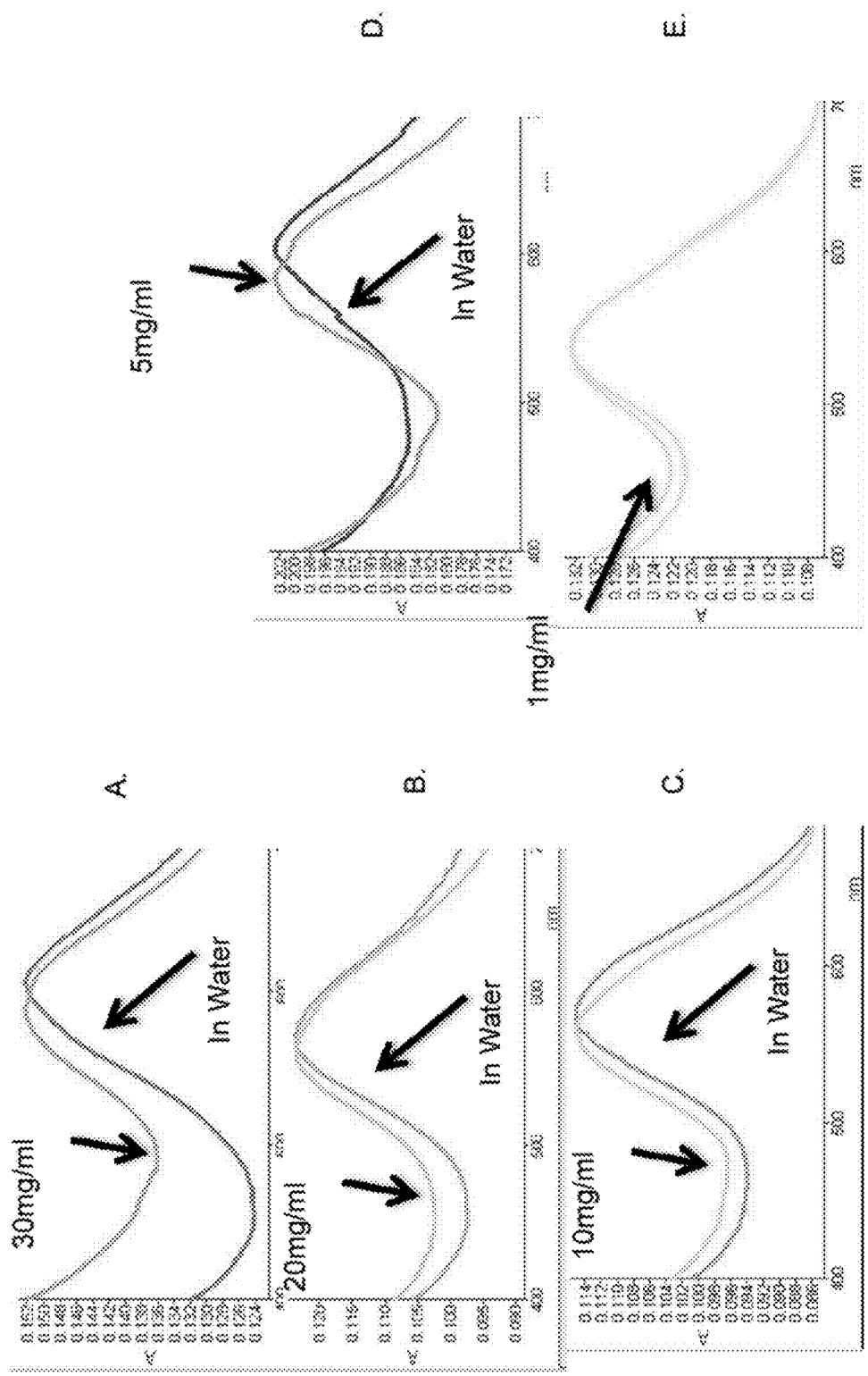
FIG. 11 illustrates graphically UV-Vis spectrum data of films in water and various glucose solutions. The film changed from a red color to an orange color upon exposure to 30 mg/ml (Plate A), from red-orange to yellow upon exposure to 20 mg/ml (Plate B), from orange to yellow upon exposure to 10 mg/ml (Plate C), from red to orange upon exposure to 5 mg/ml (Plate D), and exhibited minimal color change upon exposure to 1 mg/ml (Plate E).

Exposure to lower concentrations of glucose solution had a different effect. As seen in FIG. 11, for concentration of 30 (FIG. 11A), 20 (FIG. 11B), 10 (FIG. 11C) and 5 (FIG. 11D) mg/ml glucose solutions, the films collapsed when exposed to the glucose solution. Their color shifted towards 400 nm or the "violet" end of the spectrum. Thus, the films swelled at higher concentrations and collapsed at lower concentrations of glucose solutions.

Discussion

In order for maximal diffraction of light toward the observer, the lamellar morphology of the BCP film was oriented parallel to the glass substrate. The 3-(aminopropyl)triethoxysilane functionalization on the glass substrate interacts with the P2VP block of the BCP by influencing the morphology to be parallel to the substrate. The BCP film is then annealed by exposing it to chloroform vapor, mobilizing the polymer chains and allowing them to form the parallel lamellae.

This annealing process is relatively specific and thus precise conditions are preferably controlled. Environmental factors such as room humidity and evaporation rate of the annealing solvent may cause the BCP film to have poor morphology or break the interactions between the BCP and the substrate. It was found that low humidity, approximately 20%, and relatively slowed evaporation rate of the chloroform dramatically improved morphology. After completion of the annealing process, the BCP film was chemically functionalized by attaching 2-(bromomethyl)phenylboronic acid to the P2VP block. The BCP film was exposed to acetonitrile at an elevated temperature. However, such harsh conditions could potentially damage the BCP film or disrupt its delicate lamellar morphology.

If the lamellar morphology is disrupted by the chemical modification, then the photonic properties of the BCP film will be diminished. TEM was utilized to determine whether the lamellar morphology was maintained after functionalization with the 2-bromomethyl)phenylboronic acid.

Figure 12:
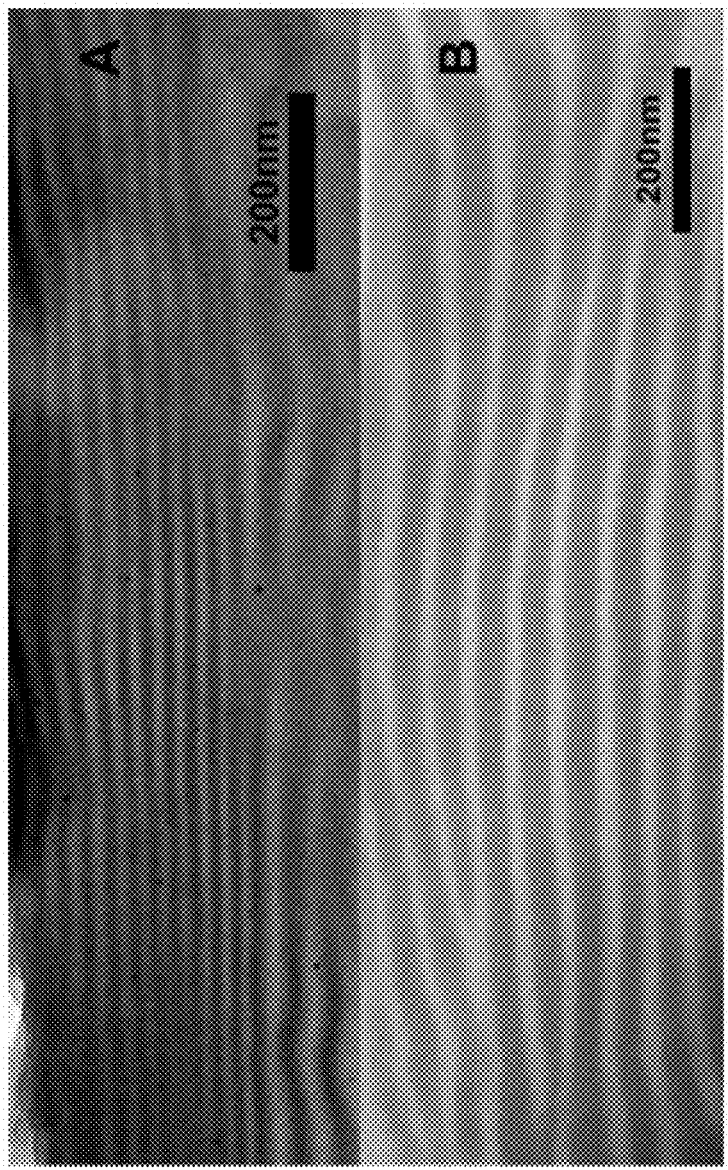
FIG. 12 illustrates transmission electron microscopy (TEM) images of annealed, unmodified PS-b-P2VP film (shown in Plate A), and of PS-b-P2VP film functionalized with 2-bromomethylphenylboronic acid exhibiting a lamellar morphology (shown in Plate B). The darker iodine stained P2VP block appears thicker due to the increased mass of the P2VP block from the functionalization as compared to the cross section seen in the unmodified film.

Referring to FIG. 12, the electron micrograph of the cross section of both an unmodified BCP film and of a BCP film functionalized with 2-(bromomethylphenylboronic acid) is presented. The lamellar morphology needed for the film's optical properties was maintained after functionalization of the P2VP block. In the unmodified film (FIG. 12A), the layer thickness of the P2VP block and PS block are similar in size as the molecular weight of each block is comparable. The iodine-stained block is the P2VP.

After chemical functionalization (FIG. 11B), the lamellar morphology was maintained. However, there is an apparent increased thickness of the darker iodine stained P2VP block versus the lighter PS block due to the increased mass added to the P2VP block from the 2-(bromomethyl)phenylboronic acid. Verification that the PS-b-P2VP films were functionalized was obtained by analyzing the chemical structure with FTIR. The pyridine group of the P2VP block substitutes the bromine in the 2-(bromomethyl)phenylboronic acid which covalently bonds the boronic acid functionalization to the pyridine. The boronic acid functionalization places a positive charge on the nitrogen atom in the pyridine ring of the P2VP block as the pyridine groups are converted to pyridinium. This conversion from pyridine to pyridinium can be observed using FTIR. The FTIR spectrum of a modified and unmodified film was taken. A peak appeared at 1627 $cm^{-1}$ in the modified film indicating the conversion of pyridine to pyridinium, or the placement of a formal positive charge on the nitrogen atom of the pyridine ring.

This functionalization serves two purposes. First, a formal positive charge is placed on the P2VP block of the BCP film, allowing it to swell in water. This swells the P2VP block to a sufficiently large thickness, which allows it to interact with visible light as dictated by Bragg's law. The second purpose of the functionalization is to introduce boronic acid to the BCP film. Boronic acid binds to sugar molecules allowing the BCP film to recognize and respond to simple sugars with a change in color. This substitution reaction was performed via exposure of the BCP film to a solution of 2-(bromomethyl)phenylboronic acid in acetonitrile while refluxing for 5 hours. This methodology could be applied for other chemical functionalizations, each with its own sensing application.

Tuning the Polymer Film Photonic Properties

Control over the optical properties or color of the BCP film allows for the production of a reliable chemical sensor. To tune the color of the functionalized BCP film, varying degrees of crosslinking were introduced into the P2VP block. The crosslinker used was 1,4-dibromo-2-butanol in conjunction with the boronic acid functionalization. The BCP was exposed to various molar ratios of 1,4-dibromo-2-butanol (crosslinker) to 2-(bromomethyl)phenylboronic acid (quaternizer). Increasing or decreasing the mole fraction of the crosslinker, allows the collapsing or swelling the polymer film in water, which tunes the color of the BCP.

Figure 13:
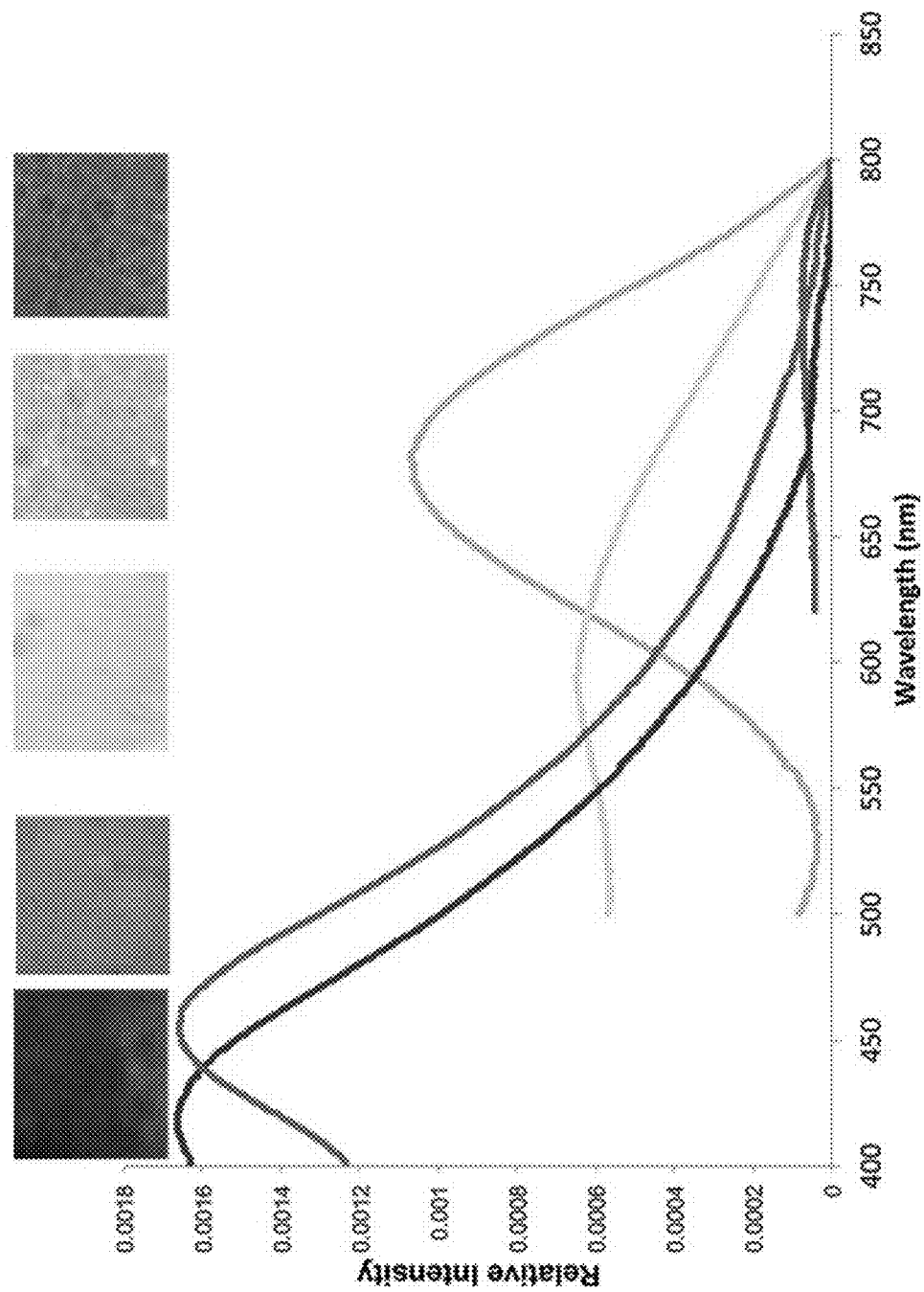
FIG. 13 illustrates graphically the colored BCP films and their corresponding visible spectra. As shown, the BCP film color can be tuned to blue, green, yellow, orange or transparent (infrared) colors depending on the degree of crosslinking. Increasing the crosslink density inhibits swelling, which blue-shifts the color of the polymer film. Each BCP film displays a different color and visible spectra depending on the molar ratio of crosslinker to quatenizer.

The BCP films may be fabricated to exhibit different colors by controlling the swelling of the polymer film through variations in crosslink density. For example, the BCP films may be tuned to blue, green, yellow, orange or infrared colors. Referring to FIG. 13, each of the colored BCP films and their corresponding visible spectra are illustrated. As shown, the BCP film's color is intense and readily recognizable visually. Thus, the need for extraneous equipment to distinguish one color from another is eliminated. This allows for the fabrication of a relatively simple sensor, which may be easily utilized by individuals and without the need for specific training to determine if the BCP film has responded to a specific analyte.

Response to Glucose

Figure 14:
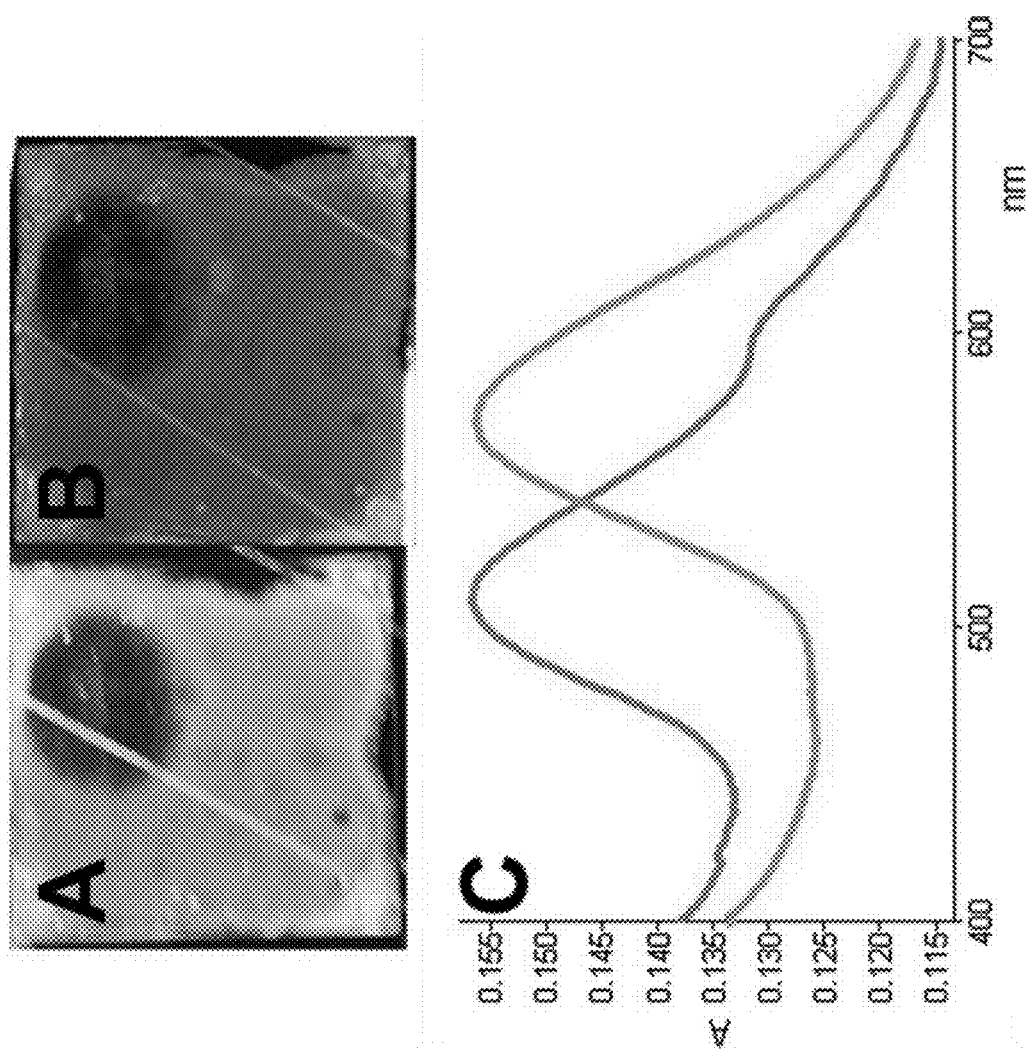
FIG. 14 illustrates the UV-Visible spectrum of the functionalized film in both water and glucose solution. When exposed to pure water, the film swelled due to the positive charge placed on the P2VP block from the functionalization (Plate A). Once immersed in a glucose solution, the functionalized polymer film swelled further due to the boronic acid groups binding glucose (Plate B). When bound to glucose, a negative charge exists on the boron atom of the boronic acid moiety, causing the film to further swell and become orange in color (Plate C). In water the film swells to reflect a peak wavelength of 510 nm, which corresponds to a color green. In the glucose solution, the film swells and reflects a peak wavelength of 590 nm, which corresponds to an orange color.

Boronic acid can bind to 1,2 and 1,3 cis diols, a chemical functionality commonly found in sugar molecules. The binding of a sugar to the boronic acid lowers its pKa. The pKa change increases the number of boronic acid residues that form the boronate complex, which is negatively charged. Such negative charge then causes the BCP film to swell, thereby changing its color. The PS-b-P2VP films functionalized with 2-(bromomethyl)phenylboronic acid were exposed to a range of concentrations of aqueous d-glucose solutions. The tested polymer films were initially green in pure deionized water due to the functionalization placing a positive charge on the P2VP block. The green films exposed to the 50 mg/ml glucose solution instantly swelled and became orange in color. This color change and UV-Visible spectrum is illustrated in FIG. 14. The shift in color was readily visible to the naked eye, and thus may be easily detected without the use of equipment such as spectrometer.

Figure 15:
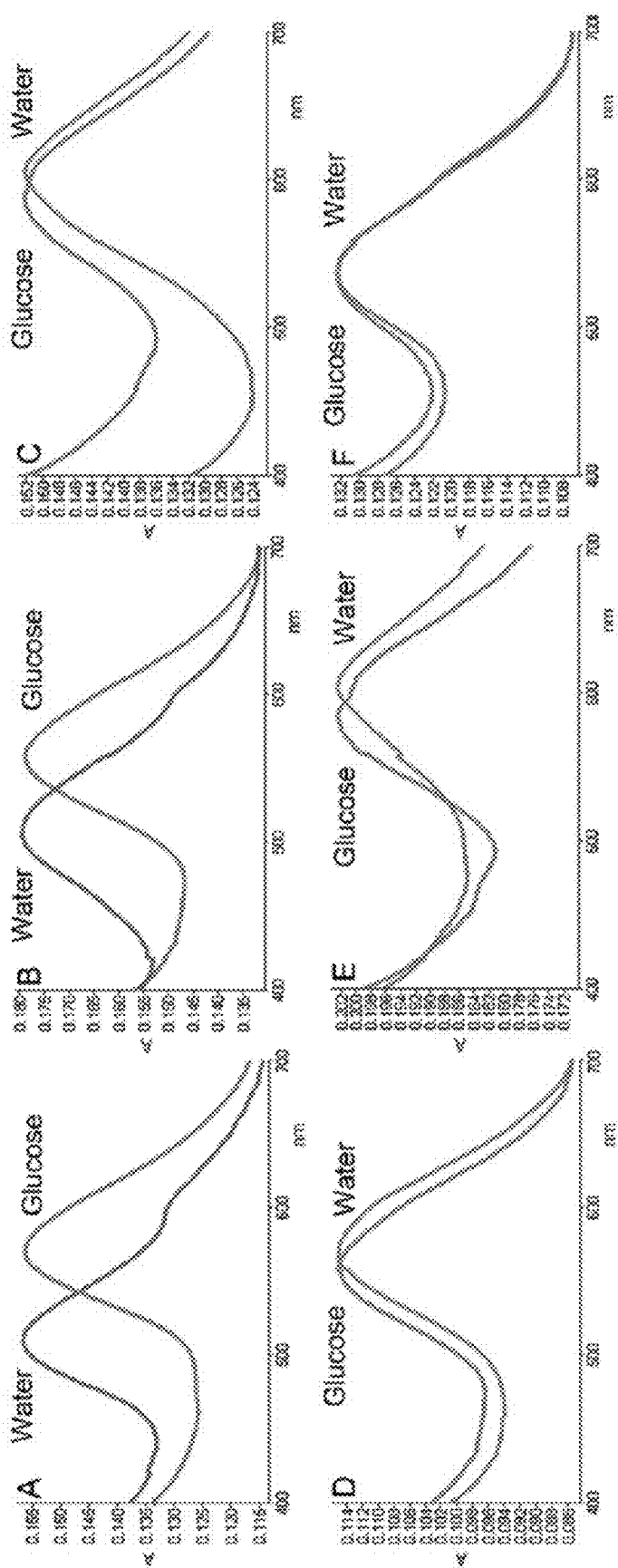
FIG. 15 illustrates graphically in graphs A-F the shift in peak wavelength of BCP samples immersed in various concentrations of glucose solution of: 50 mg/ml (A); 40 mg/ml (B); 30 mg/ml (C); 10 mg/ml (D); 5 mg/ml (E); and 1 mg/ml (F). 50 mg/ml and 40 mg/ml solutions caused an increase, or red-shift, in peak wavelength, indicating that the polymer film had swelled. However, a decrease, or blue-shift, was observed in the BCP film samples exposed to 30 mg/ml, 10 mg/ml, and 5 mg/ml solutions, indicating that the film collapsed.

Ultraviolet-visible (UV-Vis) spectroscopy was utilized to quantify the films' exposure to a range of aqueous concentrations of glucose (0-50 mg/ml). It was predicted that the spectrum peak should red-shift after exposure to glucose due to the binding and incorporation of the glucose molecule causing swelling. When exposed to concentrations of 50 mg/ml and 40 mg/ml glucose, the films shifted from green to orange or yellow, respectively, as shown in FIG. 15. This indicates that the films became swollen as expected. However, exposure to lower concentrations of glucose had a different effect.

As shown in FIG. 15, after exposure to concentrations of 30, 10 and 5 mg/ml glucose, the films blue-shifted, indicating that the polymer film had collapsed when exposed to these concentrations of glucose solution. Interestingly, this counterintuitive observation of swelling at high concentrations and collapsing at lower concentrations is provided in boronic acid detection systems.

A bi-modal response in a polymerized crystalline colloidal hydrogel system has been demonstrated. When the hydrogel was exposed to high concentrations of glucose, each boronic acid functionality bound to one glucose molecule, placing a negative charge on the boron atom which caused the film to swell and red-shift in color. Exposure to lower concentrations caused two boronic acid functionalities to bind to one glucose molecule. This effectively creates crosslinking in their hydrogel system, causing it to collapse and blue-shift in color.

Based on the results disclosed herein and illustrated in FIG. 15, a similar phenomenon is occurring in the functionalized block copolymer system. The effect of pH on phenylboronic acid's ability to bind sugars such as glucose is demonstrated. It has been shown that higher pH increases the $K_{eq}$ of the glucose binding reaction, while lower pH decreases the $K_{eq}$ of binding glucose.

Selectivity

The phenylboronic acid functionality introduced to the P2VP block of the BCP can covalently bind to any diol-containing sugar (e.g., such as glucose, fructose, mannose and galactose). The $K_{eq}$ of boronic acid binding to each one of these sugars varies depending on the sugar. This suggests that the boronic acid functionalized film should have a selective response to each simple sugar. To observe this effect, a BCP film functionalized and cross-linked to yield a blue color in water was exposed to 50 mg/ml solution of glucose, fructose, mannose, and galactose. After 30 minutes of exposure, the BCP film's visible spectra was measured using UV-Vis spectroscopy. The peak difference in wavelength was then calculated as the difference between the peak wavelength of the film in water and in the sugar solution.

Figure 16:
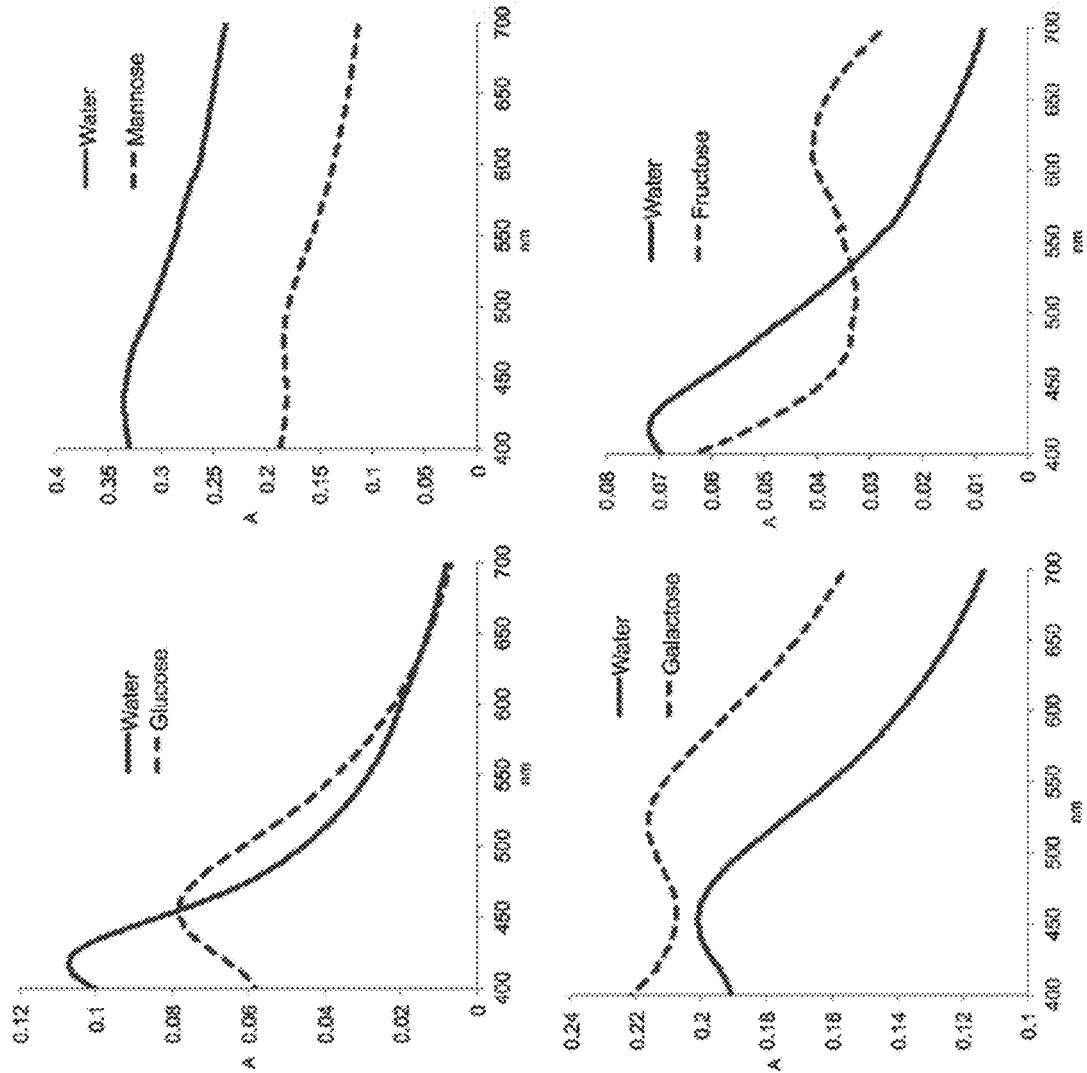
FIG. 16 illustrates graphically the shift in peak wavelength of initially tuned blue BCP films exposed to four different sugar solutions containing glucose, fructose, galactose or mannose at the same concentration. The difference of the peak wavelength observed in water versus that observed in the sugar solution was calculated to obtain the shift in wavelength. As shown, exposure to fructose induced the largest response of an approximately 200 nm red-shift in wavelength. Galactose induced a 70 nm increase in wavelength, and mannose and glucose induced smaller increases of approximately 40 nm each. This indicates that the BCP film can differentiate between fructose, galactose, mannose and glucose for a given concentration.

As shown in FIG. 16, the BCP film exposed to fructose exhibited the largest response of a 200 nm red-shift in wavelength. The film exposed to galactose exhibited a 70 nm red-shift in color. The smallest responses were those films exposed to glucose and mannose, which exhibited 44 nm and 37 nm decreases, respectively. In additional experiments, the 50 mg/ml glucose solution evoked the same shift in wavelength (see FIGS. 15A and 16), although in each case the original color of the BCP film in water was different.

This difference in response between fructose, galactose and glucose was expected. It has been reported that fructose has the highest $K_{eq}$ to bind to boronic acid, followed by galactose, and then glucose (see Springsteen, G., Wang, B. H. (2002) Tetrahedron 58(26):5291-5300). The difference in binding is due to the steric structure of each sugar. Boronic acid binds to both 1,2 and 1,3 cis diols, but preferentially binds to 1,2 cis diols. Fructose has a planar 1,2 cis diol. Glucose does not have a 1,2 cis diol, but has a 1,3 cis diol in its dominate pyranose form. Generally, glucose binds to boronic acid in its furanose form, which does contain a planar 1,2 cis diol (see Bielecki et al. (1999) Journal of the Chemical Society: Perkin Transactions 2(3):449-455). This result signifies that for a given concentration, the boronic acid functionalized BCP film can differentiate between glucose, galactose and fructose.

The binding and color change indicate that PS-b-2VP block copolymer films may be utilized for detecting a wide variety of chemical or biological targets or threats. The films functionalized with the 2-bromomethylphenylboronic acid demonstrated the ability to respond to glucose with a change in color without the use of any supplementary enzymes such as glucose oxidase. Functionalization with bromoethylamine was further modified with polyclonal ovalbumin antibodies. This film responded to the ovalbumin protein with a change in color. This concept can be further adapted for the detection of auto-inducer2 (AI-2), glycerol, Ricin or TATP.

The phenylboronic acid functionalized films can be modified to detect AI-2, which includes molecules having chemical structures isomeric to simple sugars and described as a universal signaling molecule in many types of foodborne pathogens, giving this film potential application in food packaging. This functionalization can also be used for detection of glycerol, a precursor to nitroglycerin for application in explosives detection. The protein attachment protocol can also be further modified for the attachment of peroxidase class enzymes. These enzymes can break down TATP, producing alcohols which can swell and change the color of the polymer films.

The disclosed colorimetric material system is unique in that it requires only the functionalized block copolymer to indicate an exposure to a chemical or biological target. For example, once functionalized with the 2-(bromomethyl) phenylboronic acid, the PS-b-P2VP film demonstrates the ability to respond to glucose with a change in color without the use of any supplementary enzymes such as glucose oxidase or additional equipment to assess the visible color change. The block copolymer lamellar stacks responded with a red-shift in color in high concentrations of glucose and a blue-shift in color for low concentrations of glucose. The BCP film also exhibited a selective response to fructose, glucose or galactose, by swelling to different degrees depending on which sugar is present.

The PS-b-P2VP block copolymer can easily be processed into films, sheets or other large area coatings as needed. The color of the BCP film can be tuned to blue, green, yellow or orange as demonstrated. While similar sensors exist in porous silicon, lithography and hydrogel systems, they lack the ease of fabrication and use of these block copolymer films and can require the use of a spectrometer to measure the shift in color. The results show the capabilities of photonic BCP films for chemical sensing as the functionalization can be exchanged for different sensing moieties.

All publications and patents mentioned in this specification are herein incorporated by reference to the same extent as if each individual publication or patent application was specifically and individually indicated to be incorporated by reference in its entirety. While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth.

What is claimed is:

1. A method of providing a sensor system for detecting a target analyte, comprising the steps of:
   providing a block copolymer, the block copolymer having a lamellar morphology including at least two layers;
   functionalizing the block copolymer; and
   linking an antibody to the functionalized block copolymer, wherein the antibody is capable of binding a moiety of a target analyte, and wherein the distance between the layers changes upon exposure to and selective recognition of the target analyte by the antibody so that the functionalized block copolymer exhibits a shift in peak wavelength in the visible spectrum.

2. The method of claim 1, wherein the block copolymer is 2-vinyl pyridine.

3. The method of claim 2, wherein the 2-vinyl pyridine block copolymer is functionalized with 2-bromomethylphenylboronic acid or bromoethylamine.

4. The method of claim 1, wherein the target analyte is selected from the group consisting of glucose, fructose, galactose and mannose.

5. The method of claim 1, wherein the target analyte is selected from the group consisting of a foodborne pathogen, a toxin, and an explosive compound.

6. The method of claim 5, wherein the foodborne pathogen is selected from the group consisting of *Escherichia coli*, *Listeria*, and *Salmonella*.

7. The method of claim 5, wherein the toxin is selected from the group consisting of ricin, sarin, and soman.

8. The method of claim 5, wherein the explosive compound is selected from the group consisting of nitroglycerin and triacetone triperoxide.

9. The method of claim 1, comprising the further step of coupling the functionalized block copolymer to a textile material.

* * * * *